United States Patent [19]

Parravicini

[11] Patent Number: 4,536,893
[45] Date of Patent: Aug. 27, 1985

[54] IMPLANT DEVICE FOR SUBSTAINING THE ACTIVITY OF THE MYOCARDIUM

[76] Inventor: Roberto Parravicini, Corso Genova 13, Milan, Italy

[21] Appl. No.: 669,052

[22] Filed: Nov. 7, 1984

Related U.S. Application Data

[63] Continuation of Ser. No. 387,897, Jun. 14, 1982, abandoned.

[30] Foreign Application Priority Data

Mar. 3, 1982 [IT] Italy .............................. 67241 A/82

[51] Int. Cl.³ .............................................. A61F 1/00
[52] U.S. Cl. ......................................... 623/3; 128/64; 128/1 R
[58] Field of Search .................. 3/1, 1.7; 128/1 R, 53, 128/60, 55, 64, 61, 89 R, 87 R

[56] References Cited

U.S. PATENT DOCUMENTS

| | | | |
|---|---|---|---|
| 2,826,193 | 3/1958 | Vineburg | 128/64 |
| 3,034,501 | 5/1962 | Hewson | 128/60 |
| 3,663,965 | 5/1972 | Lee, Jr. et al. | 604/175 |
| 4,192,293 | 3/1980 | Asrican | 128/1 D |
| 4,304,225 | 12/1981 | Freeman | 128/60 |

Primary Examiner—Richard J. Apley
Assistant Examiner—David J. Isabella
Attorney, Agent, or Firm—Sughrue, Mion, Zinn, Macpeak & Seas

[57] ABSTRACT

The device comprises a container housing for enveloping, at least partially, the ventricular region of the myocardium. To the inner surface of the container housing are applied membrane means which define pumping chambers between the inner surface and the myocardial wall. A pumping fluid is fed selectively to these chambers to cause expansion of the chambers and consequent compression of the myocardial wall.

5 Claims, 4 Drawing Figures

IMPLANT DEVICE FOR SUBSTAINING THE ACTIVITY OF THE MYOCARDIUM

This is a continuation, of application Ser. No. 387,897, filed June 14, 1982 now abandoned.

DESCRIPTION

The present invention relates to implant devices for sustaining the activity of the myocardium.

The attempts made until now to produce devices for sustaining or relieving the action of the myocardium can be traced back, in outline, to two basic lines of research.

The first of these is directed towards artificial devices which wholly replace the physiological organ and necessitate the actual removal of the heart itself. Such implant devices have many drawbacks, due, in particular, to the direct contact with the circulating blood and hence, to the great ease with which thromboembolisms and haemolysis can occur. This means that these devices are, in fact, only usable for very short periods and while awaiting a biological heart to replace the artificial device.

The other line of research mentioned is directed to producing devices for assisting the left ventricle only, acting as a systemic organic pump, without removing the heart. The artificial device can be either external or internal and is assembled in series along a tube provided with valves which is interposed surgically between the apex of the left ventricle and the aorta, usually abdominally. This technical solution has the same drawbacks as described above, the only difference being in the fact that, since removal of the physiological heart is not necessary, it is possible to consider re-establishing the physiological functions of this organ once the critical stage which led to the implantation of the artificial device is overcome.

In addition to the devices described, "aortic counterpulsators" are also known, which, apart from requiring the functioning of a vital artery (such as the femoral artery) to be interrupted and thus having limited times of application, are in fact only usable when functioning of the physiological heart remains above a certain minimum level.

The object of the present invention is to produce an implant device for sustaining activity of the myocardium, which will not have the drawbacks referred to above and can be fitted rapidly even under conditions of extreme urgency.

With a view to achieving this object, the present invention has as its subject a device of the aforesaid type, characterised in that it comprises:
- a container housing for at least partially enveloping the ventricular region of the myocardium,
- membrane means which are applied to the inner surface of the container housing and, in the position of enveloping the myocardium, define pumping chambers between the inner surface and the myocardial wall, and
- means for selectively feeding a pumping fluid to these chambers in order to cause expansion of the chambers and consequent compression of the myocardial wall.

By virtue of this characteristic, it is possible to produce an implant device which does not require removal of the physiological heart and, in its turn, does not need to be removed if and when the physiological activity of the heart is resumed.

The device according to the invention is generally installed by means of a sternotomy. Not being in contact with the circulating mass of blood, the device according to the invention does not cause thromboembolisms and haemolysis, and can be used for practically unlimited periods without carrying out anticoagulant treatments on the blood of the patient to whom it is fitted.

According to a preferred embodiment of the invention, the membrane means comprise separate pumping chambers acting independently on the left ventricular wall and the right ventricular wall of the myocardium.

This allows different pumping pressures to be applied to the two ventricles, and separate deactivation of the two pumping chambers when functioning of one of the natural ventricles is restored to a satisfactory level, while continuing to sustain the action of the other ventricle.

Further advantages of the invention will emerge from the following description given purely by way of non-limitative example with reference to the accompanying drawings, in which.

Figure 1:
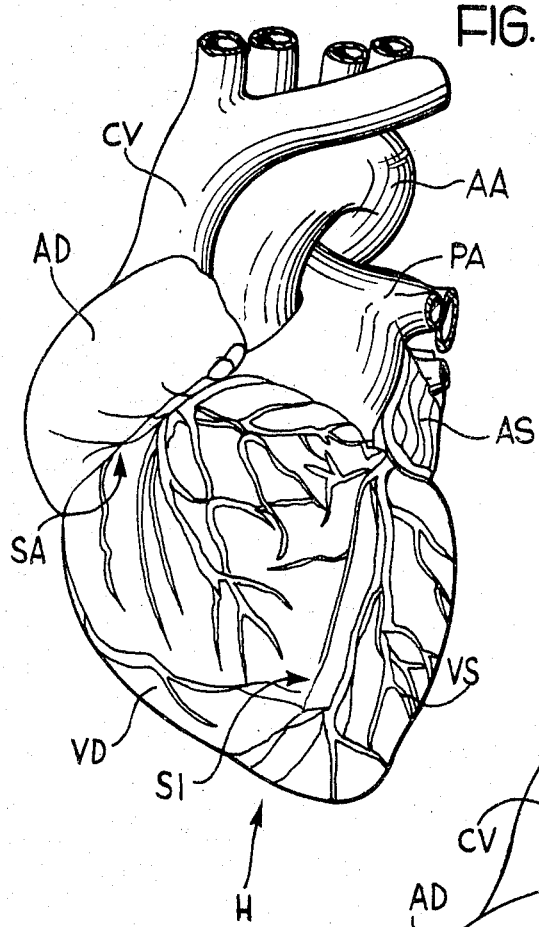
FIG. 1 is a frontal anterior view of a myocardium.

In FIG. 1, a myocardium is generally indicated H, and its right and left ventricles are shown as VD and VS respectively.

The right and left auricles of the myocardium H, are also visible in FIG. 1, being shown as AD and AS respectively.

Between the right ventricle VD and the left ventricle VS extends the interventricular sulcus, shown diagrammatically as S1.

The ventricular region VD, VS of the myocardium H is separated from the atrial region AD, AS by the atrioventricular sulcus, shown diagrammatically as SA.

The main vessels leading to the myocardium H, that is, the superior vena cava, the aorta and the pulmonary artery, are shown as CV, AA, and PA, respectively.

Figure 3:
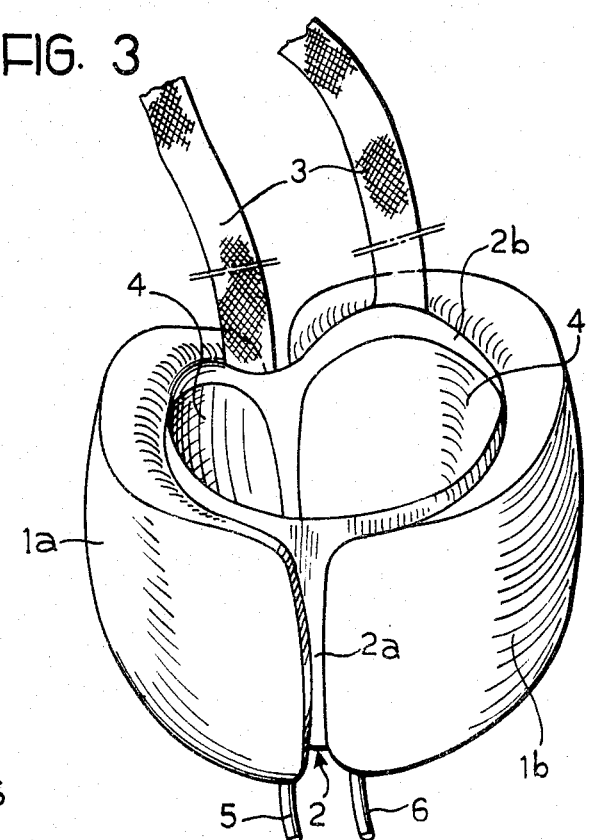
FIG. 3 is a perspective view from above, which shows diagrammatically a device according to the invention before the implantation.

As shown in FIG. 3, the device according to the invention comprises a container housing 1 consisting of two rigid or semi-rigid shells 1a, 1b connected by a deformable and inextensible connecting strip 2.

The housing 1 constitutes a sort of cap for fitting onto the ventricular region VD, VS of the myocardium H.

The container housing 1, which may also be made in the form of a net, is of biocompatible material such as titanium, metal covered in silicon or polyurethane resins, polyamides, or polytetrafluoroethylene.

The strip 2 connecting the shells 1a, 1b, on the other hand, is made from a biocompatible fabric, such as polytetrafluoroethylene or similar materials, which allows the possible connection of the strip 2 to the myocardial tissue by suturing.

As can be seen in FIG. 3, the connecting strip 2 consists of a band 2a which extends in correspondence with the interventricular sulcus S1 and a collar 2b which follows approximately the line of the atrioventricular sulcus SA.

Figure 2:
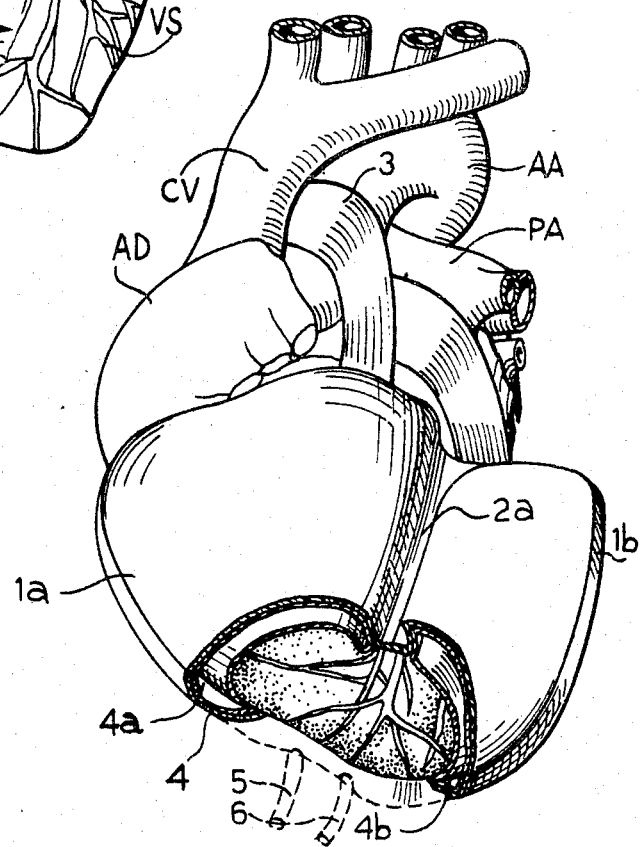
FIG. 2 shows the application of the implant device according to the invention to the myocardium of FIG. 1.

Two straps 3, which are also made from polytetrafluoroethylene or similar material, extend from the collar 2b for wrapping around the root of the aorta AA and the root of the pulmonary artery PA, so as to allow the container housing 1 to be fixed in the position in which it envelopes the ventricular region of the myocardium H (FIG. 2).

It is notable that the shape of the container housing 1 is such that it can be applied to the myocardium H without operating on any one of the main vessels CV, AA, PA which converge on the myocardium H.

This allows the device according to the invention to be implanted by a sternotomy which can be carried out even under conditions of extreme urgency (for example, by operating on a myocardium in which an infarctual episode is taking place) without necessarily having to interrupt the functioning of the organ by activating a extracorporeal circulation arrangement.

As can be seen in FIG. 2, a sac-like envelope 4 is housed within the container housing 1 and has a double wall of a biocompatible elastic membrane.

The material of the elastic membrane 4 may be selected in general from silicon resins, such as the resin known commercially as Silastic, polyurethane resins, or similar materials.

The membranous envelope 4 is divided into two chambers 4a, 4b corresponding to the two shells 1a, 1b of the container housing 1.

Figure 4:
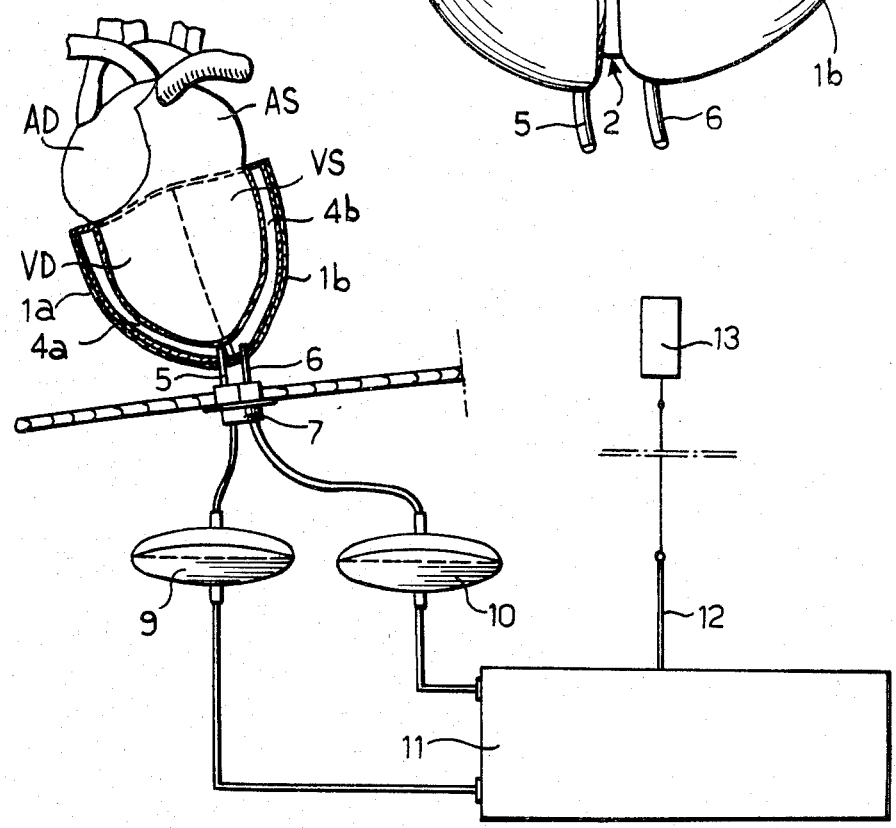
FIG. 4 shows diagrammatically the operating principle of the device according to the invention.

Respective feed tubes 5, 6 are attached to the chambers 4a, 4b and converge into a transcutaneous connector 7, shown diagrammatically in FIG. 4.

The tubes 5, 6 allow a pumping fluid, consisting of a sterile physiological liquid, to be supplied to the chambers 4a, 4b. The use of sterile liquid in the hydraulic feed circuit of the chambers 4a, 4b is to be preferred, since any possible losses from this circuit will not give rise to septic phenomena. Moreover, it is pointed out that the lack or direct contact with the circulating mass of blood renders impossible the spread of any possible infection.

The device described is such that the supply of liquid under pressure to each of the chambers 4a, 4b causes expansion of the chamber and the consequent compression of the myocardial wall.

In the example illustrated, the chamber 4a acts upon the right ventricle VD, while the chamber 4b acts upon the left ventricle VS.

The membranous envelope 4 can be stuck to the inner surface of the container housing 1 by a layer of biocompatible adhesive. Fixing between the housing 1 and the envelope 4 can also be effected by stitching, for example, in correspondence with the connecting strip 2a. Mechanical connection between the container housing 1 and the membranous envelope 4 is not strictly necessary, however, since, in its position of use, the membranous envelope 4 is confined between the myocardial wall and the inner surface of the container housing 1 which is fixed, in its turn, to the myocardium H in correspondence with the aortic root and the root of the pulmonary artery.

The ends of the feed tubes 5, 6 emerging from the body through the transcutaneous connector 7 are connected, through two interface capsules 9, 10, to an extracorporeal actuator circuit, generally indicated 11.

The actuator circuit 11 functions so as to achieve rythmic feeding of the pumping chambers 4a, 4b through the tubes 5, 6. The function of the capsules 9, 10 is to divide the pumping circuit into two branches. One of these branches extends for a substantial part within the body of the patient, and has a filling of sterile physiological liquid intended to prevent septic phenomena caused by possible losses. The other branch is extracorporeal and can have a filling of any hydraulic fluid (such as oil) for flowing around the actuator circuit.

The arrangement described is such that the conditions of pressure, flow, and volumetric displacement which takes place in the pumping chambers 4a, 4b are faithfully reproduced in the ventricular chambers VS, VD. This allows exact external control of the hydraulic parameters of the functioning of the myocardium H to which the device according to the invention is applied.

Moreover, the feed pressure of the chambers 4a, 4b may be reduced gradually as the ventricular walls regain their normal function, until the implant device is totally deactivated.

The action of sustaining the myocardium may be restarted whenever necessary, however, since the device according to the invention can be implanted into an organism for an almost unlimited period.

In the case of particularly serious myocardiac disorders, such as those which lead to making an artificial interventricular septum, or in the presence of fibrillation or tachycardia, the pumping action actuated by the actuator circuit 11 is rhythmised by a timer member in the actuator circuit 11.

In a case in which the myocardiac disorder may be attributable to an insufficient contraction of the ventricular walls, the sustaining action of the device according to the invention can be rhythmised by the myocardial muscle.

For this purpose the actuator circuit 11 is provided with a rhythmising input 12 to which is supplied a signal from a device for sensing the activity of the myocardium 13, such as an electrocardiograph, or an electrode applied to the myocardium H.

Naturally, while the principle of the invention remains the same, the details of construction and forms of embodiment may be varied widely from that described and illustrated, without going beyond the scope of the present invention.

I claim:

1. An implant device for sustaining the activity of the myocardium comprising:
    a container housing including two substantially separate rigid shells adapted to envelop the left ventricular wall and the right ventricular wall of the myocardium, respectively, and a biocompatible fabric connecting strip bridging a space formed between said shells between said shells and securely attached to said shells wherein said fabric extends in said space between said shells in correspondence with the interventricular sulcus for attachment thereto by suturing,
    membrane means secured to the inner surface of said shells defining two separate independent pumping chambers each adapted to act independently on the left ventricular wall and the right ventricular wall of the myocardium, respectively, and means for selectively and separately feeding fluid to said two chambers so as to cause expansion of the chambers and consequent compression of the left ventricular wall and the right ventricular wall of the myocardium.

2. An implant device as set forth in claim 1 wherein said membrane means is comprised of a sac-like envelope having a double wall.

3. An implant device as defined in claim 1 further comprising feed tube means connected to said pumping chambers and a transcutaneous connector connected to said feed tube means.

4. An implant device as defined in claim 1 wherein said biocompatible connecting strip fabric extends about the upper edges of said shells to define a collar adapted to extend in correspondence with the atrioventricular sulcus for attachment thereto by suturing.

5. An implant device as set forth in claim 4 wherein strap means extend from said collar for wrapping around the roots of blood vessels converging on the myocardium.

* * * * *